US009474566B2

(12) United States Patent
Paul et al.

(10) Patent No.: US 9,474,566 B2
(45) Date of Patent: Oct. 25, 2016

(54) FABRIC ELECTRODE HEAD

(71) Applicant: St. Jude Medical, Atrial Fibrillation Division, Inc., St. Paul, MN (US)

(72) Inventors: Saurav Paul, Minneapolis, MN (US); Riki Thao, Little Canada, MN (US); Hong Cao, Savage, MN (US); Kedar Ravindra Belhe, Minnetonka, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 281 days.

(21) Appl. No.: 14/076,400

(22) Filed: Nov. 11, 2013

(65) Prior Publication Data

US 2014/0066926 A1   Mar. 6, 2014

Related U.S. Application Data

(62) Division of application No. 11/618,557, filed on Dec. 29, 2006, now abandoned.

(51) Int. Cl.
| | |
|---|---|
| *A61B 18/14* | (2006.01) |
| *A61N 1/05* | (2006.01) |
| *A61B 18/16* | (2006.01) |
| *A61B 18/00* | (2006.01) |
| *A61N 1/04* | (2006.01) |

(52) U.S. Cl.
CPC .............. *A61B 18/14* (2013.01); *A61N 1/05* (2013.01); *A61B 18/16* (2013.01); *A61B 2018/00577* (2013.01); *A61N 1/0464* (2013.01)

(58) Field of Classification Search
CPC ............ A61F 2002/4495; A61F 2013/51449; A61F 2013/530664; A61F 2017/0225; A61B 2017/0225

USPC .................................................... 606/28, 41
See application file for complete search history.

(56) References Cited

U.S. PATENT DOCUMENTS

| | | | | |
|---|---|---|---|---|
| 4,709,698 | A | * | 12/1987 | Johnston et al. ............... 606/41 |
| 5,010,895 | A | * | 4/1991 | Maurer et al. ............... 607/138 |
| 5,218,973 | A | | 6/1993 | Weaver et al. |
| 5,290,281 | A | | 3/1994 | Tschakaloff |
| 5,374,283 | A | * | 12/1994 | Flick ............................... 607/46 |
| 5,643,197 | A | * | 7/1997 | Brucker et al. ................. 604/20 |
| 5,846,196 | A | * | 12/1998 | Siekmeyer et al. .......... 600/374 |
| 5,853,411 | A | * | 12/1998 | Whayne et al. ................ 606/41 |
| 5,879,348 | A | * | 3/1999 | Owens ............... A61B 18/1492 600/374 |
| 6,012,457 | A | | 1/2000 | Lesh |
| 6,210,771 | B1 | | 4/2001 | Post et al. |
| 6,327,505 | B1 | * | 12/2001 | Medhkour et al. ............. 607/99 |
| 6,443,947 | B1 | | 9/2002 | Marko et al. |
| 6,585,732 | B2 | | 7/2003 | Mulier et al. |
| 7,122,034 | B2 | | 10/2006 | Belhe et al. |

(Continued)

FOREIGN PATENT DOCUMENTS

| | | |
|---|---|---|
| JP | 2003210482 | 7/2003 |
| WO | 9716127 | 5/1997 |
| WO | 0166026 | 9/2001 |

*Primary Examiner* — Jaymi Della
(74) *Attorney, Agent, or Firm* — Marsh Fischmann & Breyfogle LLP

(57) ABSTRACT

An electrode head is disclosed that utilizes electrically conductive or dissipative fabric to exchange electrical energy with tissue. This electrode head may be used for any appropriate application, such as a catheter electrode, a return electrode, or the like. Any appropriate function may be provided by this electrode head, such as tissue ablation, tissue mapping, or providing an electrical ground.

13 Claims, 11 Drawing Sheets

(56) References Cited

U.S. PATENT DOCUMENTS

| | | | |
|---|---|---|---|
| 7,991,483 B1* | 8/2011 | Atanasoska | A61N 1/0551 607/121 |
| 2002/0148476 A1 | 10/2002 | Farley et al. | |
| 2003/0114906 A1 | 6/2003 | Booker et al. | |
| 2003/0212394 A1 | 11/2003 | Pearson et al. | |
| 2005/0267468 A1* | 12/2005 | Truckai et al. | 606/41 |
| 2006/0004353 A1* | 1/2006 | Koyfman et al. | 606/41 |
| 2006/0184165 A1 | 8/2006 | Webster et al. | |

* cited by examiner

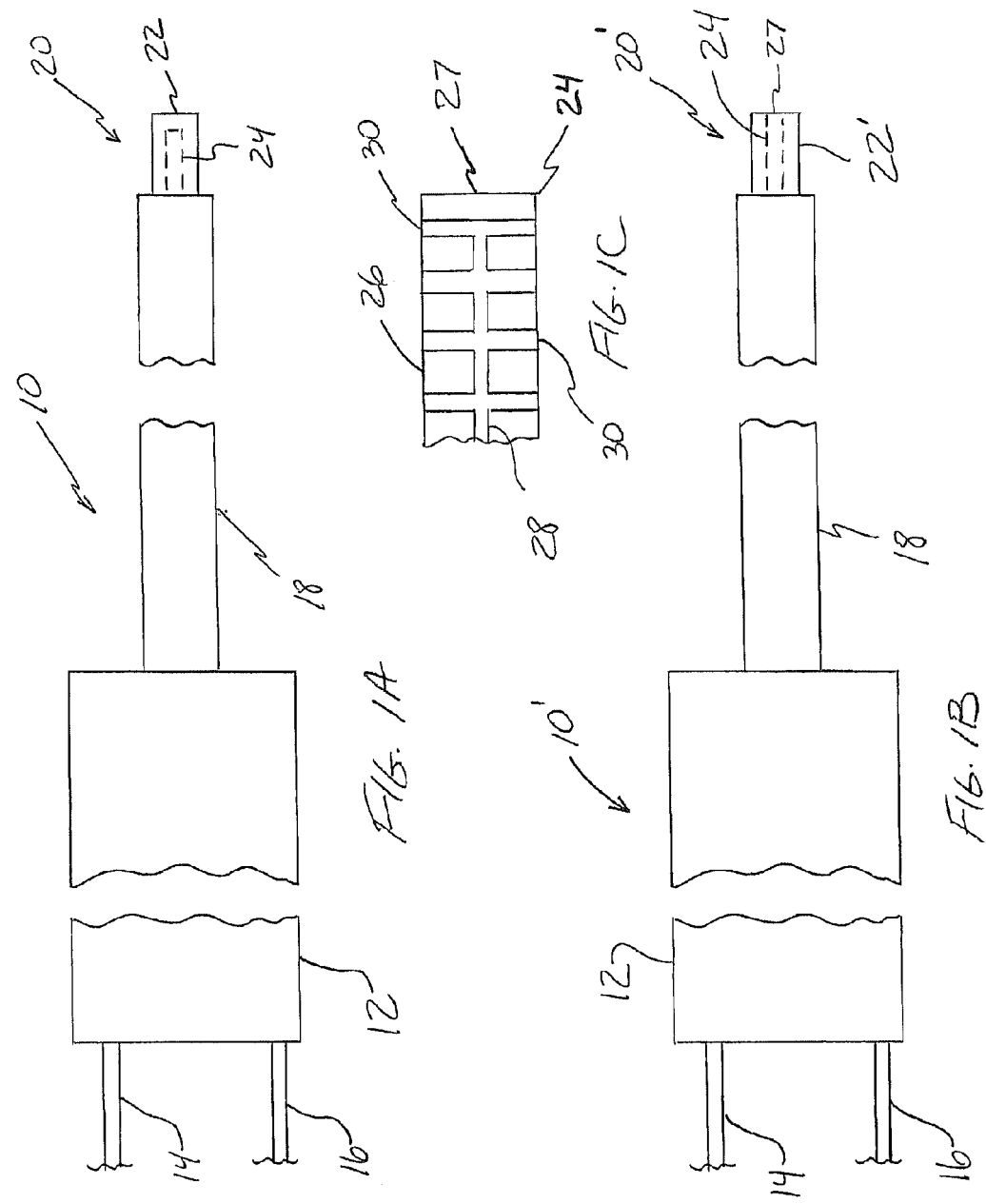

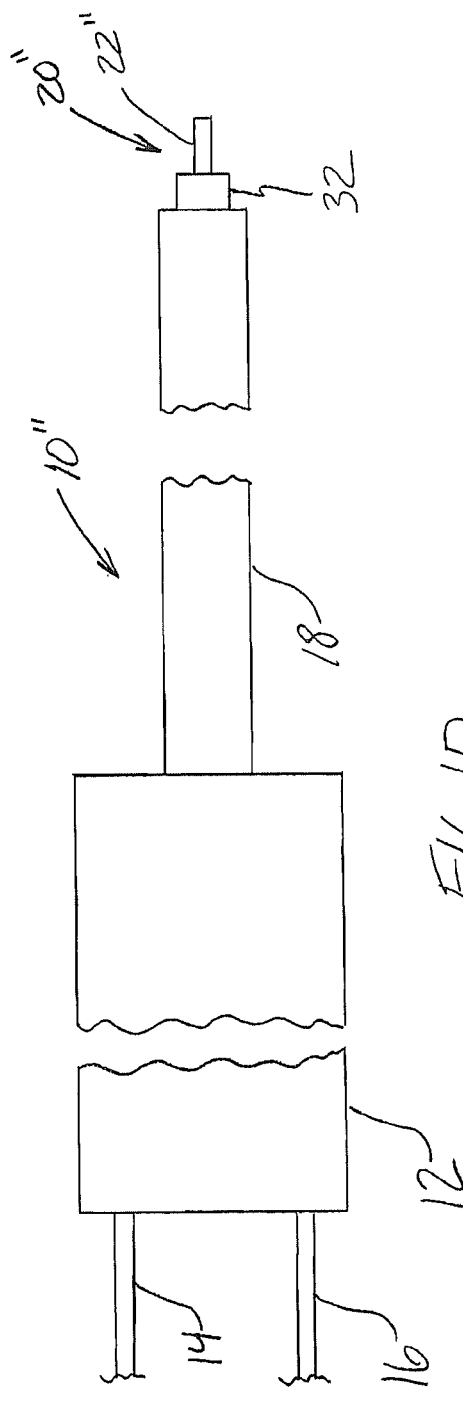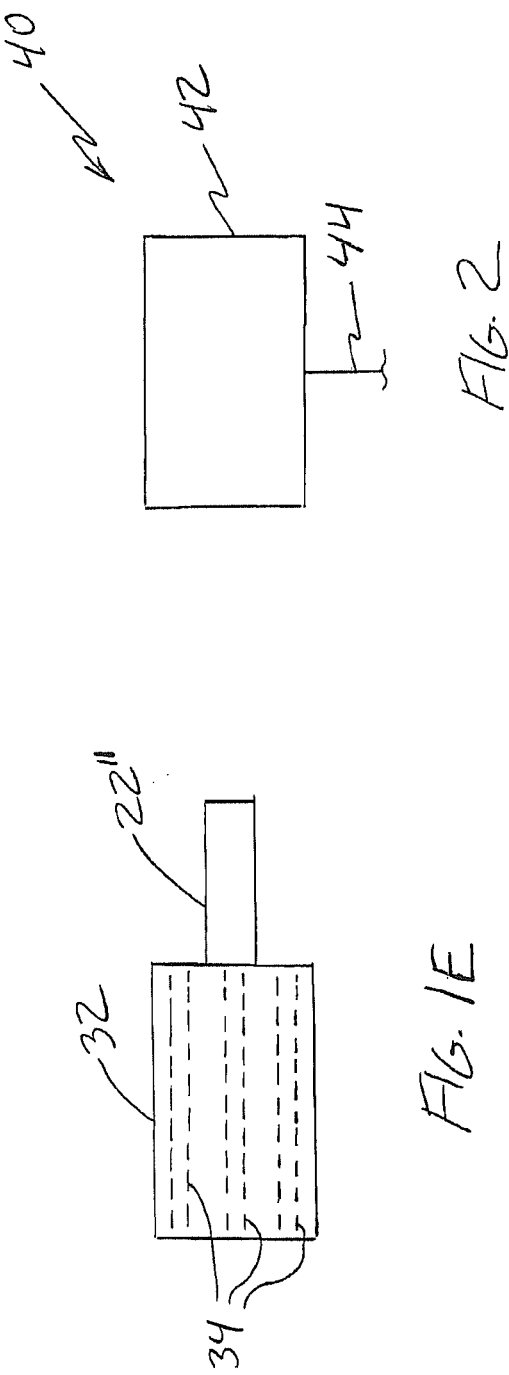

FABRIC ELECTRODE HEAD

CROSS-REFERENCE

This application is a divisional application of U.S. patent application Ser. No. 11/618,557, having a filing date of Dec. 29, 2006, now abandoned, the entire contents of which is incorporated herein by reference.

BACKGROUND OF THE INVENTION a. Field of the Invention

The instant invention generally relates to the field of electrodes. In particular, the instant invention is directed to a tissue electrode head that incorporates fabric for exchanging electrical energy with tissue.

b. Background Art

Catheters have been in use for medical procedures of many years. Catheters can be used for medical procedures to examine, diagnose, and treat while positioned at a specific location within the body that is otherwise inaccessible without more invasive procedures. During these procedures a catheter is inserted into a vessel located near the surface of a human body and is guided to a specific location within the body for examination, diagnosis, and treatment. For example, one procedure often referred to as "catheter ablation" utilizes a catheter to convey an electrical stimulus to a selected location within the human body to create tissue necrosis. Another procedure oftentimes referred to as "mapping" utilizes a catheter with sensing electrodes to monitor various forms of electrical activity in the human body.

In a normal heart, contraction and relaxation of the heart muscle (myocardium) takes place in an organized fashion as electrochemical signals pass sequentially through the myocardium from the sinoatrial (SA) node located in the right atrium to the atrialventricular (AV) node and then along a well defined route which includes the His-Purkinje system into the left and right ventricles. Sometimes abnormal rhythms occur in the atrium which are referred to as atrial arrhythmia. Three of the most common arrhythmia are ectopic atrial tachycardia, atrial fibrillation, and atrial flutter. Arrhythmia can result in significant patient discomfort and even death because of a number of associated problems, including the following: (1) an irregular heart rate, which causes a patient discomfort and anxiety; (2) loss of synchronous atrioventricular contractions which compromises cardiac hemodynamics resulting in varying levels of congestive heart failure; and (3) stasis of blood flow, which increases the vulnerability to thromboembolism. It is sometimes difficult to isolate a specific pathological cause for the arrhythmia although it is believed that the principal mechanism is one or a multitude of stray circuits within the left and/or right atrium. These circuits or stray electrical signals are believed to interfere with the normal electrochemical signals passing from the SA node to the AV node and into the ventricles. Efforts to alleviate these problems in the past have included significant usage of various drugs. In some circumstances drug therapy is ineffective and frequently is plagued with side effects such as dizziness, nausea, vision problems, and other difficulties.

An increasingly common medical procedure for the treatment of certain types of cardiac arrhythmia and atrial arrhythmia involves the ablation of tissue in the heart to cut off the path for stray or improper electrical signals. Such procedures are performed many times with an ablation catheter. Typically, the ablation catheter is inserted in an artery or vein in the leg, neck, or arm of the patient and threaded, sometimes with the aid of a guidewire or introducer, through the vessels until a distal tip of the ablation catheter reaches the desired location for the ablation procedure in the heart. The ablation catheters commonly used to perform these ablation procedures produce lesions and electrically isolate or render the tissue non-contractile at particular points in the cardiac tissue by physical contact of the cardiac tissue with an electrode of the ablation catheter and application of energy. The lesion partially or completely blocks the stray electrical signals to lessen or eliminate arrhythmia.

One difficulty in obtaining an adequate ablation lesion using conventional ablation catheters is the constant movement of the heart, especially when there is an erratic or irregular heart beat. Another difficulty in obtaining an adequate ablation lesion is caused by the inability of conventional catheters to obtain and retain uniform contact with the cardiac tissue across the entire length of the ablation electrode surface. Without such continuous and uniform contact, any ablation lesions formed may not be adequate.

It is well known that benefits may be gained by forming lesions in tissue if the depth and location of the lesions being formed can be controlled. In particular, it can be desirable to elevate tissue temperature to around 50° C. until lesions are formed via coagulation necrosis, which changes the electrical properties of the tissue. For example, when sufficiently deep lesions are formed at specific locations in cardiac tissue via coagulation necrosis, undesirable ventricular tachycardias and atrial flutter may be lessened or eliminated. "Sufficiently deep" lesions means transmural lesions in some cardiac applications.

One difficulty encountered with existing ablation catheters is assurance of adequate tissue contact. Current techniques for creating continuous linear lesions in endocardial applications include, for example, dragging a conventional catheter on the tissue, using an array electrode, or using pre-formed electrodes. All of these devices comprise rigid electrodes that do not always conform to the tissue surface, especially when sharp gradients and undulations are present, such as at the ostium of the pulmonary vein in the left atrium and the isthmus of the right atrium between the inferior vena cava and the tricuspid valve. Consequently, continuous linear lesions can be difficult to achieve. With a rigid catheter, it can be difficult to maintain sufficient contact pressure until an adequate lesion has been formed. This problem is exacerbated on contoured or trabecular surfaces. If the contact between the electrode and the tissue cannot be properly maintained, a quality lesion may not be formed.

There are additional issues relating to some current ablation electrode designs. Certain ablation electrodes may char tissue and/or cause coagulation in a very short time, even when being operated in a low-power mode. Ablation electrodes may of course be operated in a high-power mode as well. The resulting elevated temperature of the ablation electrode itself may also have an adverse effect on the ablation electrode. In this regard, at least some ablation electrodes offer fluid cooling. Relatively high flow rates (e.g., 70 ml per minute) are typically used for these ablation electrodes to provide an effective cooling. This may be disadvantageous in one or more respects. Moreover, the flow ports are prone to becoming blocked and/or obstructed, which of course has an adverse effect on the ability of the fluid to cool the ablation electrode to the desired temperature. In this regard, increased contact pressure between the ablation electrode and the target tissue may be used to increase the potential for realizing an adequate electrical coupling, but this may increase the potential for flow port blockage and/or obstruction. Reduced contact pressures may reduce the potential for flow port blockage and/or obstruction, but this may degrade the electrical coupling between the ablation electrode and the tissue since the cooling fluid exiting the ablation electrode may become diluted by bodily fluids.

BRIEF SUMMARY OF THE INVENTION

Various aspects of the present invention that will be addressed herein relate to a tissue electrode head—an electrode head that is intended to at least electrically interface with tissue (e.g., while in contact with or when spaced from the tissue). Each such tissue electrode head may be characterized as exchanging electrical energy with the tissue at the desired time. Generally, the tissue electrode head may be of any appropriate type. For instance, the tissue electrode head may be in the form of a catheter electrode. Another option is for the tissue electrode head to be in the form of a ground patch or the like that interfaces with the patient's skin (e.g., interfaces with an exterior surface of the patient). The tissue electrode head may also provide any appropriate function or combination of functions. One embodiment has the tissue electrode head in the form of an active electrode to provide a desired function (e.g., tissue ablation; tissue mapping; electrical energy source). Another embodiment has the tissue electrode head in the form of a return electrode to provide an electrical ground. The electrode head may apply electrical energy to a single location (e.g., for spot tissue ablation), or may apply electrical energy to tissue while being moved relative to the tissue (e.g., to create a linear lesion). Furthermore, the tissue electrode head may be of either a "dry" configuration or of a "wet" configuration that provides a flow of an appropriate fluid by/through the electrode head as desired. The various electrode heads to be described herein also may be appropriate for other types of electrodes as well. Finally, each of the following aspects may be used in combination with one or more of the other aspects.

A first aspect of the present invention is generally directed to a tissue electrode head. This electrode head includes a fabric. At least part of this fabric is electrically conductive, and may be electrically interconnected with an appropriate electrical energy source. When the electrode head is disposed in an appropriate position relative to a patient, electrical energy may be exchanged with patient tissue via the fabric.

The fabric for the electrode head can be porous. In one embodiment, the fabric has a porosity within a range from being impervious to a particular fluid used with the electrode head, to providing the fluid with an unimpeded flow. Fabric porosity may be utilized to achieve a desired flow rate through the electrode head (e.g., for a wet electrode configuration that will be discussed below). Another option is to utilize a fabric porosity that achieves a desired degree of fluid retention. The porosity of the electrode head may also have an impact on the electrical behavior of the electrode head. The fabric may also be characterized as being flexible, for instance to provide a desired interface with the patient tissue (e.g., undulating and/or curved surfaces). In one embodiment, the fabric has a modulus of elasticity of no more than about that of the target tissue. However, the fabric could be incorporated as a rigid structure as well.

Generally, the construction/configuration of the fabric may be tailored/engineered to accomplish one or more desired objectives, for instance to provide a desired electrical field to in turn provide a desired electrical interaction with patient tissue. For instance, in some cases it may be desirable to provide a substantially constant electrical conductivity along the length of the electrode head. In other instances, it may be desirable to provide a graded electrical conductivity along at least a portion of the length of the electrode head in at least some respect (e.g., a certain length segment may be more electrically conductive than another length segment). One or more sensors may be incorporated into the electrode head to monitor the performance of the electrode head in at least some respect (e.g., a thermal sensor to monitor the electrode head/patient tissue interface temperature; a pressure sensor to monitor the contact between the electrode head and patient tissue; a fiber optic or ultrasound sensor for in situ lesion identification and/or characterization).

The fabric for the electrode head may be configured in any appropriate manner. For instance, the fabric may be in the form of an at least generally flat or planar structure (e.g., for a ground patch or return electrode application). The fabric may also be formed into a hollow structure or shell having a closed distal end. Another option would be to wrap the fabric into an at least generally cylindrical structure. The fabric may also be in the form of a plurality of cantilevered structures. Each of these cantilevered structures may be of any appropriate configuration, for instance flat or planar structures, at least generally cylindrical structures, or the like. The electrode head also may be configured to compress or deflect to a degree when brought into engagement with patient tissue, or to at least substantially retain its configuration at all times.

The entirety of the fabric may be electrically conductive or electrically dissipative. Another option is for the fabric to include some combination of electrically conductive materials (e.g., electrically conductive materials being those having a conductivity of at least about $10^{-2}$ S/m (Siemens per meter) in one embodiment), electrically dissipative materials (e.g., electrically dissipative materials being those having a conductivity of at least about $10^{-9}$ S/m in one embodiment), and electrically non-conductive materials (e.g., electrically non-conductive materials being those having a conductivity of less than about $10^{-9}$ S/m in one embodiment). Any appropriate electrically conductive material may be used by the fabric, any appropriate electrically dissipative material may be used by the fabric, and any appropriate electrically non-conductive material may be used by the fabric. In one embodiment, the electrically non-conductive material is in the form of a dielectric material.

The fabric may be defined by a plurality of first threads or thread segments and a plurality of second threads or thread segments, where each first thread is electrically conductive or dissipative, and where each second thread is electrically non-conductive. In one embodiment, each first thread is defined by a plurality of conductive or dissipative filaments that are wrapped or twisted together, while each second thread is defined by a plurality of non-conductive filaments that are wrapped or twisted together. In any case, the various first threads and the various second threads each may be disposed in orientations or woven together in a manner that generates a desired electrical field for transferring electrical energy to patient tissue and/or that provides one or more desired properties for the electrode head. The following characterizations may apply individually or in any combination: 1) the plurality of first threads and the plurality of second threads may be disposed in different orientations; 2) the plurality of first threads may extend at least generally along a length dimension of the tissue electrode head, or stated another way parallel to a reference axis associated with a length dimension of the electrode head; 3) the plurality of second threads may be wrapped about a reference axis associated with a length dimension of the electrode head (e.g., in combination with item number 2); 4) at least some of the second threads may extend at least generally along a length dimension of the tissue electrode head, or stated another way parallel to a reference axis associated with a length dimension of the tissue electrode head (e.g., in combination with item number 2); and 5) each of the plurality of first threads and each of the plurality of second threads may be wrapped about a reference axis associated with a length dimension of the tissue electrode head, for instance at different wrap angles.

The fabric may be defined by multiple yarns or yarn segments, where each yarn is defined by twisting a plurality of threads together along a length dimension of the corresponding yarn. Generally, the features discussed herein with regard to threads is equally applicable to yarns. In one embodiment, at least one yarn is electrically conductive or dissipative, while at least one yarn is electrically non-conductive. The fabric may utilize yarns of a common stiffness, or at least one yarn used by the fabric may have a different stiffness than at least one other yarn used by the fabric. Furthermore, the fabric may utilize yarns having the same denier (diameter) and thread count, or at least one yarn used by the fabric may have a different denier (diameter) and/or thread count compared to at least one other yarn utilized by the fabric. The denier and/or thread count of one or more yarns of the fabric may be utilized to control the porosity of the fabric, which in turn may be utilized to affect a flow of fluid through the fabric (e.g., for a "wet" electrode head configuration and as will be discussed below), may be used to establish/affect the electrical behavior of the electrode head, or both.

The electrode head may include a plurality of layers—any appropriate number of layers may be utilized. Adjacent layers may be disposed in interfacing and/or spaced relation. At least one of these layers will include a fabric defined by one or more materials that are electrically conductive or dissipative. In one embodiment, first and second layers are disposed in interfacing relation, where the first layer incorporates the fabric. The first layer may be electrically conductive or dissipative, while the second layer may be electrically non-conductive. One embodiment has the first layer (electrically conductive or dissipative) being incorporated by the electrode head so as to be positioned closer to the patient tissue than the second layer (electrically non-conductive). Another embodiment has the second layer (electrically non-conductive) being incorporated by the electrode head so as to be positioned closer to the patient tissue than the first layer (electrically conductive or dissipative). The second layer may be formed from any appropriate material or combination of materials, such as a dielectric. Moreover, the second layer may be of any appropriate type, such as a fabric or a non-fabric construction.

The fabric of the electrode head may include multiple segments in the length dimension, and that have one or more different properties. For instance, the fabric may include first and second segments. The first segment may be electrically conductive or dissipative, while the second segment may be electrically non-conductive. One embodiment has the first segment (electrically conductive or dissipative) being disposed distally relative to the second segment (electrically non-conductive). The first segment may define a distal end or distal tip of the electrode head. Another embodiment has the second segment (electrically non-conductive) being disposed distally relative to the first segment (electrically conductive or dissipative). The second segment may define a distal end or distal tip of the electrode head.

The electrode head may include a distal end section, where this distal end section includes a plurality of fabric segments that are each in the form of a cantilever (e.g., a structure having a fixed end and a free end). Each of these fabric segments may be disposed in any appropriate orientation, including relative to each other. In one embodiment, at least some of the fabric segments are disposed in different orientations (e.g., in non-parallel relation to each other). In another embodiment, a least some of the fabric segments diverge relative to a reference axis proceeding toward their respective fabric segment distal end (e.g., a "fanned out" configuration). The plurality of fabric segments may collectively define a splayed configuration for the electrode head as well.

The tissue electrode head may be of a "dry" configuration or may be of a "wet" configuration. In the latter regard, a flow of an appropriate fluid may be provided past and/or through the electrode head, and which may interface with the fabric. As noted above, the fabric may be characterized as being porous. The porosity of the fabric may have an effect on the flow of fluid through the electrode head. The fluid flowing through the electrode head in turn may have an effect on the electrical and/or thermal characteristics of the electrode head. Since the electrical and thermal characteristics of the electrode head have an effect on a lesion formed during RF ablation, the fabric may be tailored/engineered to obtain a desired lesion. For instance, it may be desirable to utilize a higher thread count at a proximal end of the electrode head (e.g., "proximal" being in a direction of a handle that may be associated with the tissue electrode head) compared to a distal end of the electrode head (e.g., "distal" being in a direction proceeding away from a handle that may be associated with the tissue electrode head). Increasing the thread count should decrease the porosity of the fabric.

Although any appropriate flow rate may be utilized for the case of a wet electrode configuration, a flow rate of no more than about 30 ml/minute may be sufficient in at least certain instances to accomplish one or more objectives based upon the electrode head incorporating fabric. Representative objectives include cooling the electrode head and providing a desired degree of hydraulic conductivity. For instance, a flow of fluid may be provided past a conductive portion of the electrode head, and this fluid may then carry the current to the tissue (e.g., to provide a virtual electrode). This allows the electrode head to utilize a distal end that is electrically non-conductive and/or for the tip of the electrode head to be spaced from the patient tissue and still be capable of providing an adequate electrical coupling via the fluid flow. A substantially constant hydraulic conductivity may exist along the length of the electrode head, or the hydraulic conductivity may be graded along at least a portion of the length of the electrode head (e.g., increasing progressing toward a distal end of the electrode head). A graded hydraulic conductivity may be achieved by modifying the porosity of the electrode head and/or incorporating an anisotropically conductive fabric into the electrode head.

Any appropriate way of providing a fluid flow to/through the electrode head may be utilized. For instance and as will be discussed in more detail below, the fabric may be wrapped around what may be characterized as a core, plug, or mandrel. This core may be porous to allow fluid injected therein to flow radially outwardly through the fabric. Another option would be to include one or more internal flow channels or the like in the core and that terminate on an exterior surface of the core that interfaces with the fabric. The core may be formed from any appropriate material or combination of materials, may be electrically conductive, electrically dissipative, or electrically non-conductive, and may be rigid or flexible. It should be appreciated that the core may be utilized for a dry electrode configuration as well.

A second aspect of the present invention is generally directed to a tissue electrode head that incorporates a plurality of electrode segments. Each of these electrode segments includes a distal tip that is engageable with patient tissue. At least some of these electrode segments are disposed or are disposable in different orientations relative to each other.

The electrode head may be electrically interconnected with any appropriate electrical energy source (e.g., an RF generator). When the electrode head is disposed in an appropriate position relative to a patient, electrical energy may be transferred to patient tissue via one or more of the electrode segments. Although each of the electrode segments may receive a common electrical signal, such may not be required in all instances (e.g., some of the electrode segments may not receive any electrical signal; one or more electrode segments could receive one electrical signal, while one or more other electrode segments could receive a different electrical signal).

At least some of the electrode segments may be in the form of fabric, and in one embodiment each such electrode segment is defined entirely by or at least incorporates fabric. Therefore, relevant portions of the discussion presented above with regard to the first aspect may be utilized by this second aspect. However, other materials may be utilized to define the electrode segments as well. Although each electrode may be formed from a common material, in one embodiment at least one of the electrode segments is formed from one material and at least one electrode segment is formed from a different material.

Each of the electrode segments may be in the form of a cantilever—a structure having a fixed end and an oppositely disposed free end (the above-noted distal tip). At least some of the electrode segments may be characterized as diverging from each other proceeding toward their respective electrode segment distal tip. The plurality of electrode segments also may be characterized as collectively defining a splayed configuration for the electrode head.

The various electrode segments may be characterized as being flexible or bendable. In one embodiment, each electrode segment has a modulus of elasticity of no more than about that of the target tissue. Although each of the electrode segments may be of a common stiffness, one or more electrode segments may be of a different stiffness than one or more other electrode segments. Although the various electrode segments may be disposed in equally spaced relation, a varying distribution of the electrode segments may be utilized as well. Stated another way, the electrode head may include a uniform density of electrode segments or a non-uniform density of electrode segments.

A third aspect of the present invention is generally directed to a tissue electrode head that incorporates a plurality of electrode segments that are disposed in end-to-end relation, and where at least two of these electrode sections have different diameters.

Any appropriate number of electrode segments may be utilized. In one embodiment, a smaller diameter electrode segment is more distally disposed than a larger diameter electrode segment. In another embodiment, the smallest diameter electrode segment defines a distal end section of the electrode head, while one or more other larger diameter electrode segments are more proximally disposed.

The electrical conductivity may differ between two or more of the electrode segments. One embodiment has the electrical conductivity change from electrode segment to electrode segment. Further in this regard, the electrical conductivity may increase on an electrode segment-by-electrode segment basis proceeding in the direction of the distal tip of the electrode head. Another embodiment has the most distally disposed of the electrode segments being of the highest electrical conductivity compared to the other electrode segment(s).

One or more of the electrode segments may be electrically conductive or electrically dissipative, including having each electrode segment be electrically conductive or dissipative. One or more of the electrode segments may be electrically non-conductive. At least one conductive or dissipative electrode segment and at least one non-conductive electrode segment may be utilized. Therefore, the features discussed below in relation to the fourth aspect may be used by this third aspect as well. Each electrode segment may be formed from any appropriate material or combination of materials. In one embodiment, at least one electrically conductive or dissipative electrode segment incorporates electrically conductive or dissipative fabric, although each of the electrode segments could incorporate fabric. Therefore, the features discussed above in relation to the first aspect may be used by this third aspect as well individually or in any combination. The features to be discussed in relation to the fifth, sixth, and seventh aspects may be used by this third aspect as well, individually or in any combination.

A fourth aspect of the present invention is generally directed to a tissue electrode head that incorporates a plurality of electrode segments that are disposed in end-to-end relation. At least one of these electrode segments is electrically non-conductive, while at least one of these electrode segments is electrically conductive or electrically dissipative. At least one of the electrode segments utilizes fabric.

Any appropriate number of electrode segments may be utilized. In one embodiment, a non-conductive electrode segment is more distally disposed than a conductive or dissipative electrode segment, including where a non-conductive electrode element defines a distal tip of the electrode head. In another embodiment, a conductive or dissipative electrode segment is more distally disposed than a non-conductive electrode segment, including where this conductive or dissipative electrode element defines a distal tip of the electrode head and includes fabric.

Each electrode segment may be formed from any appropriate material or combination of materials. In one embodiment, at least one electrically conductive or dissipative electrode segment utilizes electrically conductive or dissipative fabric, although each of the electrode segments may utilize fabric. Therefore, the features discussed above in relation to the first aspect may be used by this fourth aspect as well, individually or in any combination. One or more of the electrode segments may have a different outer diameter than at least one other electrode segment. Therefore, the features discussed above in relation to the third aspect may be used by this fourth aspect as well individually or in any combination. The features to be discussed in relation to the fifth, sixth, and seventh aspects may be used by the fourth aspect as well, individually or in any combination.

A fifth aspect of the present invention is generally directed to a tissue electrode head that incorporates a plurality of electrode segments that are disposed in end-to-end relation. An electrically non-conductive electrode segment defines a distal tip of the electrode head, while at least one more proximally disposed electrode segment is electrically conductive or electrically dissipative. The various features discussed above in relation to the first, third, and fourth aspects, as well as the sixth and seventh aspects to be discussed below, may be used in relation to this fifth aspect, individually or in any combination.

A sixth aspect of the present invention is generally directed to a tissue electrode head. The electrical conductivity of the electrode head, the hydraulic conductivity of the electrode head, or both, is different at least at two different locations along a length dimension of the electrode head. The various features discussed above in relation to the first, third, fourth, and fifth aspects, as well as the seventh aspect to be discussed below, may be used in relation to this sixth aspect, individually or in any combination.

A seventh aspect of the present invention is generally directed to a tissue electrode head. The porosity of the electrode head is different at least at two different locations along a length dimension of the electrode head. The various features discussed above in relation to the first, third, fourth, fifth, and sixth aspects may be used in relation to this seventh aspect, individually or in any combination.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 1A illustrates one embodiment of a catheter electrode system having an electrode head that incorporates an electrically conductive/dissipative fabric.

FIG. 1B illustrates another embodiment of a catheter electrode system having an electrode head that incorporates an electrically conductive/dissipative fabric.

FIG. 1C illustrates one embodiment of a core about which an electrically conductive/dissipative fabric may be wrapped for an electrode head, and which includes a plurality of fluid flowpaths.

FIG. 1D illustrates another embodiment of a catheter electrode system having an electrode head that incorporates an electrically conductive/dissipative fabric.

FIG. 1E is an enlarged view of the electrode head of FIG. 1D, along with one configuration of a base for providing a fluid to the electrode head.

FIG. 2 is a plan view of one embodiment of a patch electrode that utilizes an electrically conductive/dissipative fabric.

DETAILED DESCRIPTION

Figure 3A:
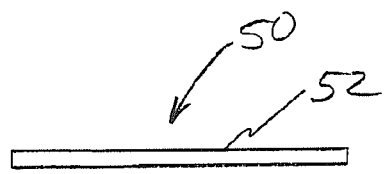
FIG. 3A illustrates a single layer of an electrically conductive/dissipative fabric that may be used to define an electrode head.

Various embodiments of electrodes that utilize at least one fabric section for a corresponding electrode head will now be described, where at least part of this fabric section is electrically conductive or electrically dissipative. An electrically conductive portion of a fabric section is one having an electrical conductivity of at least about $10^{-2}$ S/m in one embodiment. An electrically dissipative portion of a fabric section is one having an electrical conductivity of at least about $10^{-9}$ S/m. Any such fabric section may include the following features, individually or in any appropriate combination: 1) a fabric section may be defined by one or more threads, where each such thread is a collection of filaments that are twisted together along a length dimension of the thread; 2) a fabric section may be defined by one or more yarns, where each such yarn is a collection of threads that are twisted together along a length dimension of the yarn; 3) a fabric section may be defined by threads/yarns of different diameters; 4) a fabric section may be defined by threads having different filament counts, by yarns having different thread counts, or both; 5) a fabric section may be formed from any appropriate material or combination of materials; 6) a fabric section may be of any appropriate size, shape, and/or configuration; 7) a fabric section may be in the form of a solid structure; 8) a fabric section may be in the form of a hollow structure; 9) a fabric section may be in the form of an at least substantially rigid structure; 10) a fabric section may be in the form of a flexible structure; 11) a fabric section may have a modulus of elasticity of no more than about that of the target tissue (e.g., the myocardial wall) in one embodiment; 12) a fabric section may be in the form of a porous structure; 13) a fabric section may have a variable porosity depending on the application, may have a porosity within a range of being impervious to a particular fluid used with the electrode head, to providing such a fluid with an unimpeded flow in one embodiment, or both; 14) a fabric section may have one or more regions with different porosities; 15) a fabric section may be used in combination with one more other layers or sections to define an electrode head; 16) a fabric section may be integrated with an electrode head and/or configured to provide a desired electrical field and/or a desired interaction with patient tissue; 17) a fabric section may provide/accommodate a substantially constant electrical conductivity along the length of the electrode head; 18) a fabric section may provide/accommodate a varied electrical conductivity along the length of the electrode head; 19) a fabric section may provide/accommodate a substantially constant hydraulic conductivity along the length of the electrode head; and 20) a fabric section may provide/accommodate a varied hydraulic conductivity along the length of the electrode head. Although these electrode heads are particularly suited for tissue applications, where electrical energy is exchanged between the electrode head and tissue, they may be utilized by any appropriate electrode and for any appropriate application.

FIG. 1A illustrates one embodiment of what may be characterized as a tissue electrode system 10—an electrode system that is intended to mechanically interface or at least electrically couple with tissue. Initially, the tissue electrode system 10 may be operatively interconnected with one or more other components, such as a navigation display, an imaging system, an electrical energy source, or the like. The tissue electrode system 10 is illustrated as being in the form of a catheter electrode that may be introduced into a patient's artery or vein at an appropriate location (e.g., the leg, neck, or arm). Additional components may be utilized to direct the tissue electrode system 10, more specifically its electrode head 20, to the desired location within the patient's body (e.g., a guidewire or introducer).

The tissue electrode system 10 includes a handle 12 (e.g., disposed outside of the patient's body), an elongated body 18 (e.g., a catheter or other device, and disposable within a patient's body) that can be attached to the handle 12, and an electrode head 20. Other components of the tissue electrode system 10 include a fluid conduit 14 and an electrical conduit 16. Each of the fluid conduit 14 and the electrical conduit 16 may be of any appropriate size, shape, and/or configuration. Generally, the fluid conduit 14 provides an appropriate fluid to the electrode head 20 as desired (e.g., through a lumen or the like), while the electrical conduit provides an appropriate electrical signal to and/or from the electrode head 20 as desired. Incorporation of the fluid conduit 14 by the tissue electrode system 10 provides a wet electrode configuration. The fluid conduit 14 also may be eliminated, providing a dry electrode configuration for the tissue electrode system 10 (not shown).

The electrode head 20 includes at least a fabric section 22, which may be of any appropriate size, shape, and/or configuration. The entirety of the electrode head 20 may be defined by the fabric section 22. Another option is for the fabric section 22 to be disposed about and/or mounted on what may be characterized as an internal core 24. That is, the core 24 is optional and is thereby represented by dashed lines in FIG. 1A. In the case of the tissue electrode system 10 of FIG. 1A, the core 24 is encased by the fabric section 22. This need not always be the case. FIG. 1B illustrates an alternative electrode head 20' for a tissue electrode system 10', where its fabric section 22' does not cover a distal end wall 27 of the core 24. Common components between the embodiments of FIGS. 1A and 1B are identified by the same reference numeral, and the discussion presented herein is applicable to these components in each embodiment. Those corresponding components that differ in at least some respect are identified by a "single prime" designation. Various other embodiments disclosed herein utilize a core having a distal segment that is exposed.

The core 24 may: 1) be of any appropriate size, shape, and/or configuration; 2) be formed from any appropriate material or combination of materials; 3) be in the form of a rigid structure or a flexible structure; and/or 4) provide any appropriate function or combination of functions in relation to the electrode head 20/20'. For instance, the core 24 may provide a mounting structure for the fabric section 22/22' (e.g., for integrating the fabric section 22/22' with the electrode head 20/20'). The core 24 may also be utilized for directing fluid through the fabric section 22/22' for a wet electrode application. One option would be for the core 24 to be in the form of a solid structure that is sufficiently porous such that a fluid flow directed into the core 24 via the fluid conduit 14 would pass through the fabric section 22/22' at a desired flow rate. Another option would be for the core 24 to include one or more internal fluid conduits 28 (FIG. 1C) that extend to an external surface of the core 24, such as its sidewall 26, distal end wall 27, or both. The intersection of a fluid conduit 28 with the exterior of the core 24 defines a port 30. Each port 30 may be of any appropriate size, shape, and/or configuration. The core 24 may include any appropriate number of ports 30, and multiple ports 30 may be disposed in any appropriate arrangement.

FIG. 1D illustrates another variation of the tissue electrode system 10 of FIG. 1A. Common components between the embodiments of FIGS. 1A and 1D are identified by the same reference numeral, and the foregoing discussion remains applicable to these components. Those corresponding components that differ in at least some respect are identified by a "double prime" designation. In the case of the tissue electrode system 10" of FIG. 1D, the electrode head 20" includes a fabric section 22" that cantilevers or extends from what may be characterized as a base 32. This base 32 is appropriately integrated with the body 18, may be of any appropriate size, shape, and/or configuration, may be formed from any appropriate material or combination of materials, and as shown in FIG. 1E includes one or more fluid conduits or lumens 34 that receive a fluid from the fluid conduit 14. Each fluid conduit 34 may be of any appropriate size, shape, and/or configuration, and multiple fluid conduits may be disposed in any appropriate arrangement.

The tissue electrode systems of the embodiments of FIGS. 1A, 1B, and 1D are each in the form of catheter electrodes, and each such catheter electrode may be used to provide any appropriate function or combination of functions (e.g., tissue ablation; tissue mapping; return electrode). A tissue electrode system whose electrode head incorporates a fabric section may also be used for external tissue applications, such as in the case of the patch electrode 40 of FIG. 2. The patch electrode 40 includes a fabric section 42, and which may be attached to a patient's skin at any appropriate location and in any appropriate manner (e.g., by use of any acceptable adhesive or fastening band). An appropriate electrical conduit 44 (e.g., a wire or cable) is electrically interconnected with this fabric section 42. The patch electrode 40 may also be irrigated.

Figure 3B:
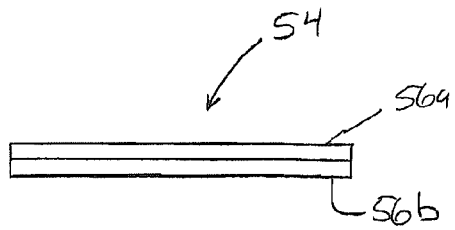
FIG. 3B illustrates a pair of layers that may be utilized to define an electrode head, where at least one of these layers is an electrically conductive/dissipative fabric.
Figure 3C:
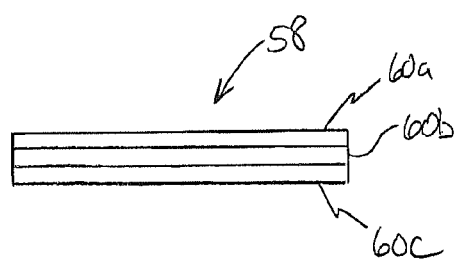
FIG. 3C illustrates three layers that may be utilized to define an electrode head, where at least one of these layers is an electrically conductive/dissipative fabric.

FIGS. 3A-F are directed to various representative configurations of electrode heads that utilize at least one fabric section. FIG. 3A illustrates an electrode head 50 having a single fabric section 52 that may be of any appropriate size, shape, and/or configuration. FIG. 3B illustrates an electrode head 54 having a pair of sections or layers 56a, 56b that are disposed in interfacing relation and each of which may be of any appropriate size, shape, and/or configuration. At least one of the sections 56a, 56b may be formed from a fabric that is electrically conductive or electrically dissipative. The other of these sections 56a, 56b may also be electrically conductive (to the same extent, to a greater extent, or to a lesser extent), may be electrically dissipative, or may be electrically non-conductive. The other of these sections 56a, 56b also may be in the form of a fabric, or may be of any other appropriate form. FIG. 3C illustrates an electrode head 58 having at least three sections or layers 60a, 60b, 60c that are disposed in interfacing relation and each of which may be of any appropriate size, shape, and/or configuration. At least one of the sections 60a, 60b, 60c may be formed from a fabric that is electrically conductive or electrically dissipative. The other of these sections 60a, 60b, 60c may also be electrically conductive (to the same extent, to a greater extent, or to a lesser extent), dissipative, or non-conductive. The other of the sections 60a, 60b, 60c also may be in the form of a fabric, or may be of any other appropriate form. Generally, any number of sections or layers may be utilized to define an electrode head, and where at least one of these sections or layers is fabric. Although adjacent layers may be disposed in interfacing relation, such may not be required in all instances. Moreover, single or multi-layer configurations may exist in any appropriate configuration.

Figure 3D:
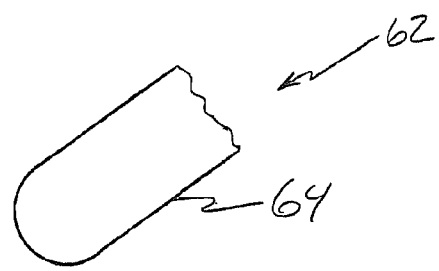
FIG. 3D illustrates one embodiment of fabric that has been formed into a hollow, three-dimensional shape for an electrode head.
Figure 3E:
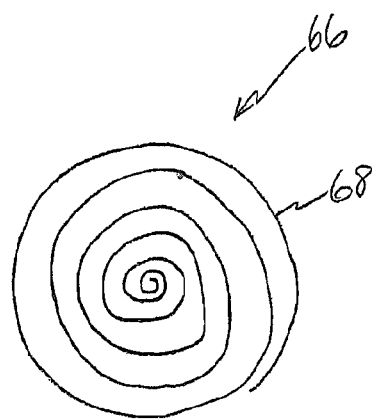
FIG. 3E is an end view of an electrically conductive/dissipative fabric that has been wrapped to define an electrode head.
Figure 3F:
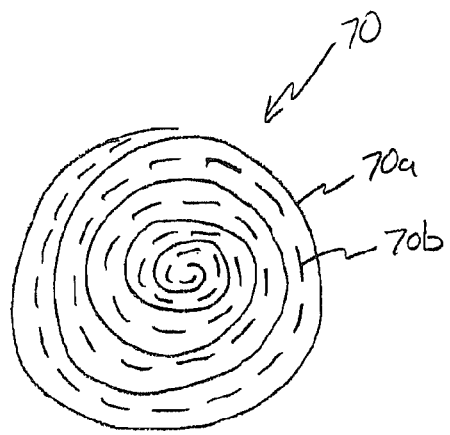
FIG. 3F is an end view of multiple layers that have been wrapped to define an electrode head, and where at least one of these layers is an electrically conductive/dissipative fabric.

FIG. 3D illustrates an electrode head 62 having at least a fabric section 64. This fabric section 64 may be a solid structure or may be a hollow structure. The fabric section 64 may be of any appropriate size, shape, and/or configuration. FIG. 3E illustrates an electrode head 66 where a single fabric section or layer 68 has been rolled up into an at least generally cylindrical configuration. Although a space is shown between each adjacent pair of wraps, such need not be the case. Finally, FIG. 3F illustrates an electrode head 70 having at least two sections or layers 72a, 72b that have been rolled up into an at least generally cylindrical configuration. Again, although a space is shown between each adjacent pair of wraps, such need not be the case. At least one of the layers 72a, 72b may be formed from a fabric that is electrically conductive or electrically dissipative. The other of these sections or layers 72a, 72b may also be electrically conductive (to the same extent, to a greater extent, or to a lesser extent), may be electrically dissipative, or may be electrically non-conductive. The other of these sections or layers 72a, 72b also may be in the form of a fabric, or may be of any other appropriate form. Single or multi-layer configurations could also be folded into a desired end configuration (e.g., bellows-like).

Figure 4:
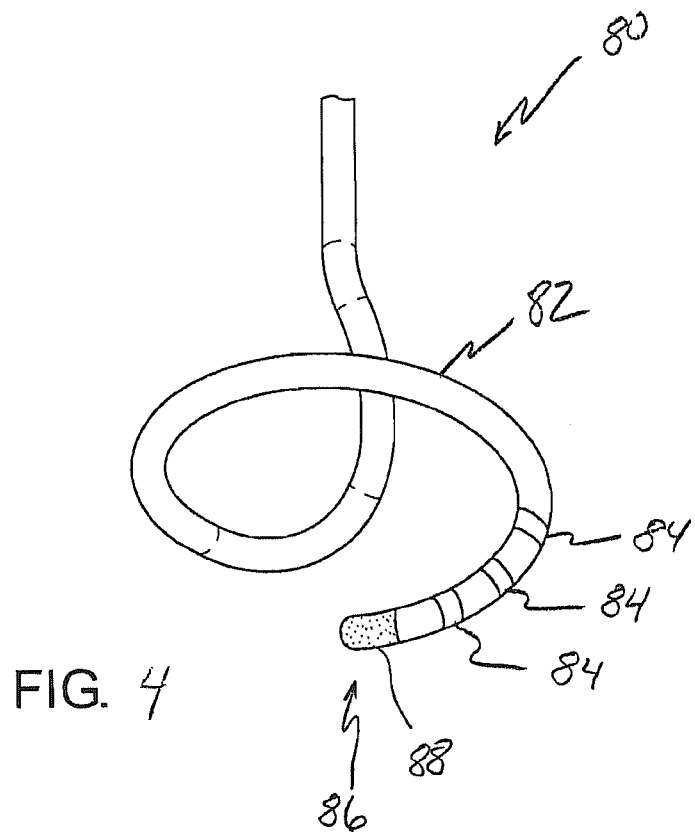
FIG. 4 is a perspective view of one embodiment of an electrode system having an electrode head that incorporates an electrically conductive/dissipative fabric and that also utilizes a plurality of proximally disposed ring electrode elements.

FIG. 4 illustrates a portion of another embodiment of a tissue electrode system 80. The tissue electrode system 80 includes an elongated body 82 that may be interconnected with an appropriate handle (e.g., handle 12 in FIG. 1A). The body 82 is sufficiently flexible to be directed through a bodily passageway (e.g., a vein or artery). There are a number of ring electrode elements 84 that are spaced along the length dimension of the body 82. An electrode head 86 is also provided at the distal end of the body 82. This electrode head 86 includes a fabric section 88.

FIGS. 5-13 illustrate various embodiments of electrode heads that incorporate fabric for exchanging electrical energy with patient tissue (e.g., transmitting electrical energy for active electrode applications; receiving electrical energy for passive electrode applications). Each of these electrode heads may be utilized by any appropriate tissue electrode system, and may be adapted as desired/required for the corresponding tissue electrode system application. For instance, each of these electrode heads could be utilized by any of the tissue electrode systems of FIGS. 1A, 1B, 1D, 2, and 4. Each of these electrode heads may be used with or without a core (e.g., core 24). The fabric section of a given electrode head may cover only a portion of the core, or may enclose at least a portion of the core (e.g., at least generally in accordance with the tissue electrode 10 of FIG. 1A). It will be appreciated that any feature of any of these electrode heads may be used by any of the other electrode heads as well, where appropriate.

Certain components are illustrated in relation to each of the electrode heads of FIGS. 5-13. Each is shown in conjunction with a body 92 having an outer section 94 and an inner section 96, and the space therebetween may be characterized as a lumen. This body 92 has a length dimension that extends along a reference axis 98. Although the reference axis 98 is illustrated as being linear, the body 92 will typically be flexible for being directed through a bodily passageway and as shown in FIG. 4. An electrical conduit 100 of any appropriate type (e.g., a wire or cable) is schematically illustrated and extends along the body 92 for electrical interconnection with an electrically conductive/dissipative portion of the relevant electrode head. An arrow 102 indicates a direction of fluid flow between the inner section 96 and outer section 94 of the body 92 (e.g., a wet electrode configuration), while representative fluid flow arrows may be illustrated regarding the exiting of this fluid flow through the electrode head. Any appropriate way of providing a fluid flow to the relevant electrode head may be utilized. Moreover, each of the electrode heads may be utilized without any fluid flow (e.g., in a dry electrode configuration).

Figure 5:
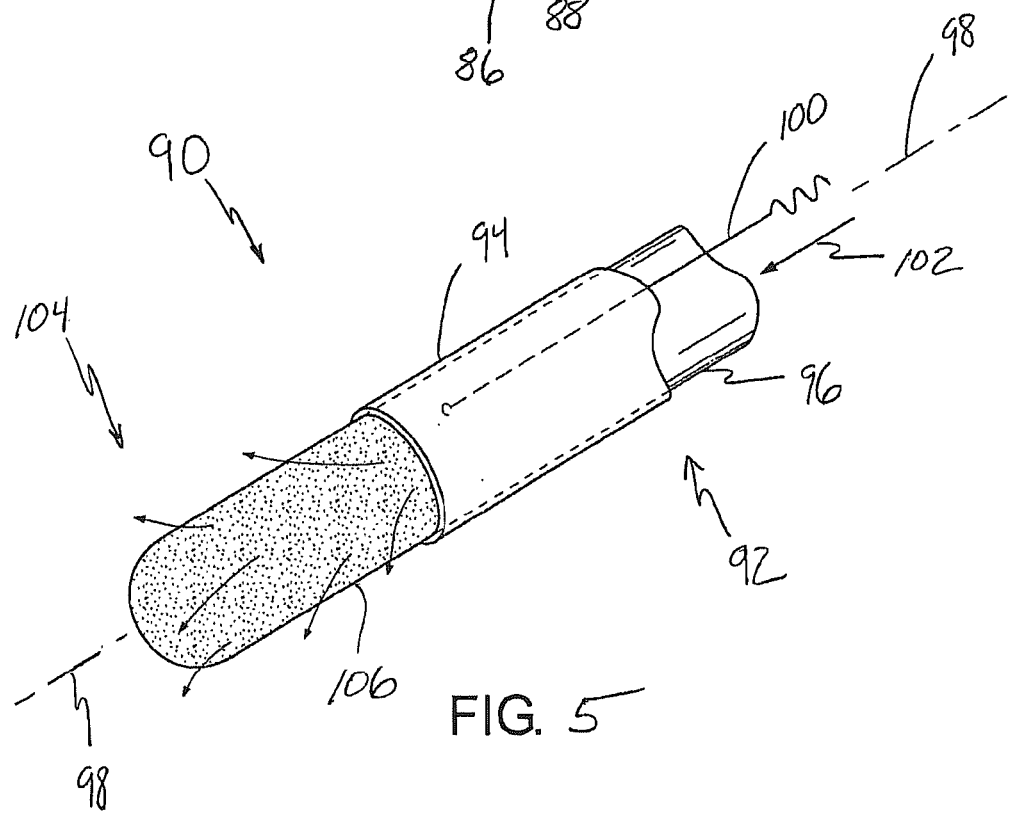
FIG. 5 is a perspective view of one embodiment of an electrode head that incorporates an electrically conductive/dissipative fabric and that accommodates a fluid flow for a wet electrode configuration.

The tissue electrode system 90 of FIG. 5 includes an electrode head 104 that incorporates a fabric section 106. The fabric section 106 again may be disposed over a core (e.g., core 24 from FIG. 1A, core 114 introduced below in relation to FIG. 6A), may be in the form of a hollow structure, or may be in the form of a solid structure. Various other representative electrode head configurations that incorporate fabric for controlling/affecting the exchange of electrical energy with tissue will now be addressed in relation to the embodiments of FIGS. 6-13.

Figure 6A:
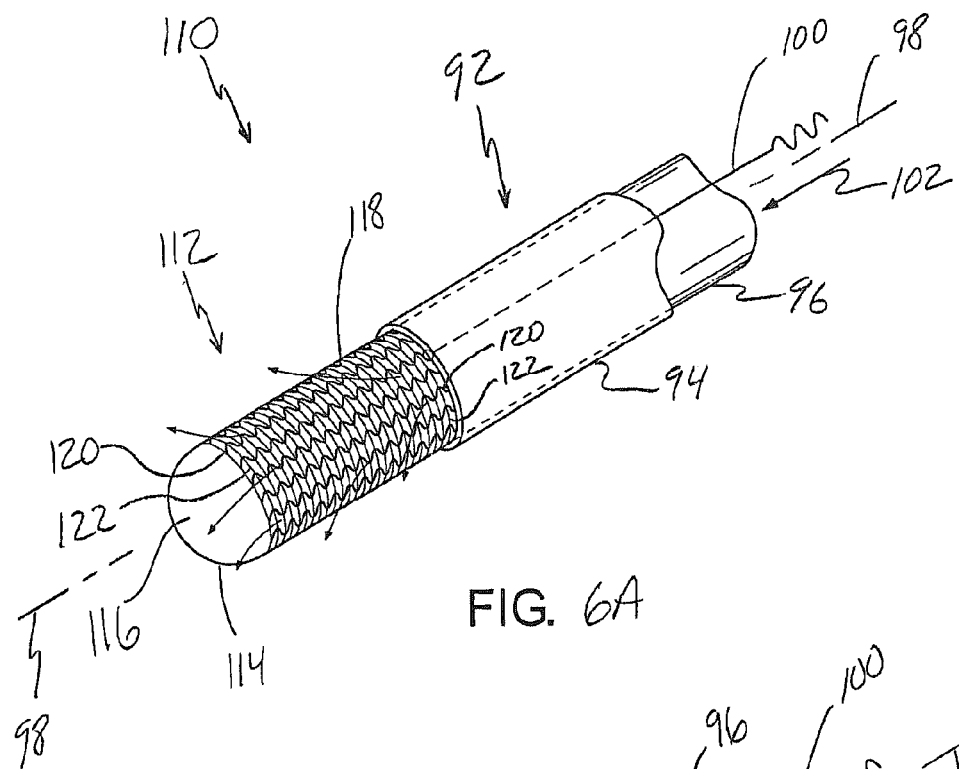
FIG. 6A is a perspective view of one embodiment of an electrode head that incorporates a plurality of electrically conductive/dissipative thread/yarn segments that extend at least generally along the length dimension of the electrode head, along with a plurality of electrically non-conductive thread/yarn segments that are wrapped about an axis that corresponds with a length dimension of the electrode.

The tissue electrode system 110 of FIG. 6A includes an electrode head 112. There are two main components of the electrode head 112—a fabric section 118 and a core 114. Generally, the fabric section 118 is disposed about the core 114 over only a portion of its length. As such, a tip 116 of the core 114 is exposed. This tip 116 is illustrated as having a rounded configuration. Other configurations may be appropriate for the tip 116 as well. The discussion presented above with regard to the core 24 is equally applicable to the core 114, and will not be repeated. In accordance with the foregoing, the fabric section 118 could also cover the tip 116 of the core 114, and the fabric section 118 could be used without the core 114. The length or amount of the core 114 that is exposed may be modified from that illustrated in FIG. 6A as well. Finally, segments of exposed portions of the core 114 could be spaced along the reference axis 98 (e.g., by having the fabric section 118 be wrapped about the core 114 at a plurality of locations that are spaced along the reference axis 98). Each of these permutations is applicable to the various embodiments disclosed herein, with the exception of the FIG. 12A embodiment.

The fabric section 118 used by the electrode head 112 includes what may be characterized as a plurality of first yarn or thread segments 120 that are electrically conductive or electrically dissipative, as well as what may be characterized as a plurality of the second yarn or thread segments 122 that are electrically non-conductive. Generally, the various first yarn segments 120 are disposed in one orientation, while the various non-conductive second yarn segments 122 are disposed in a different orientation. Further in this regard and for the illustrated embodiment, the first yarn segments 120 extend at least generally linearly or axially along the length dimension of the electrode head 112 (e.g., at least generally parallel with the reference axis 98, or so as to define the warp of the fabric section 118), while the non-conductive second yarn segments 122 are disposed or wrapped about the reference axis 98 and thereby cross or intersect with the first yarn segments 120 (e.g., so as to define the weft of the fabric section 118). The various first yarn segments 120 and the various second yarn segments 122 are woven together to define the fabric section 118 (e.g., illustrated by the squiggly lines defining the first yarn segments 120).

Figure 6B:
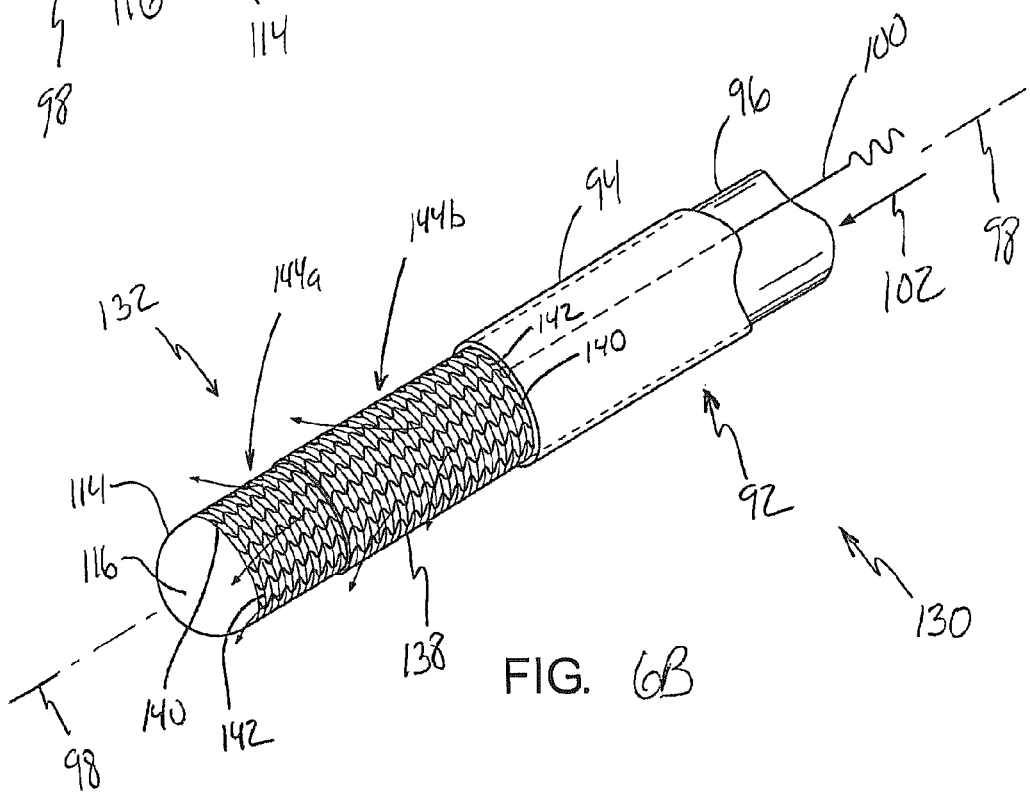
FIG. 6B is a variation of the electrode head of FIG. 6A, where the electrode head utilizes a stepped configuration.
Figure 12A:
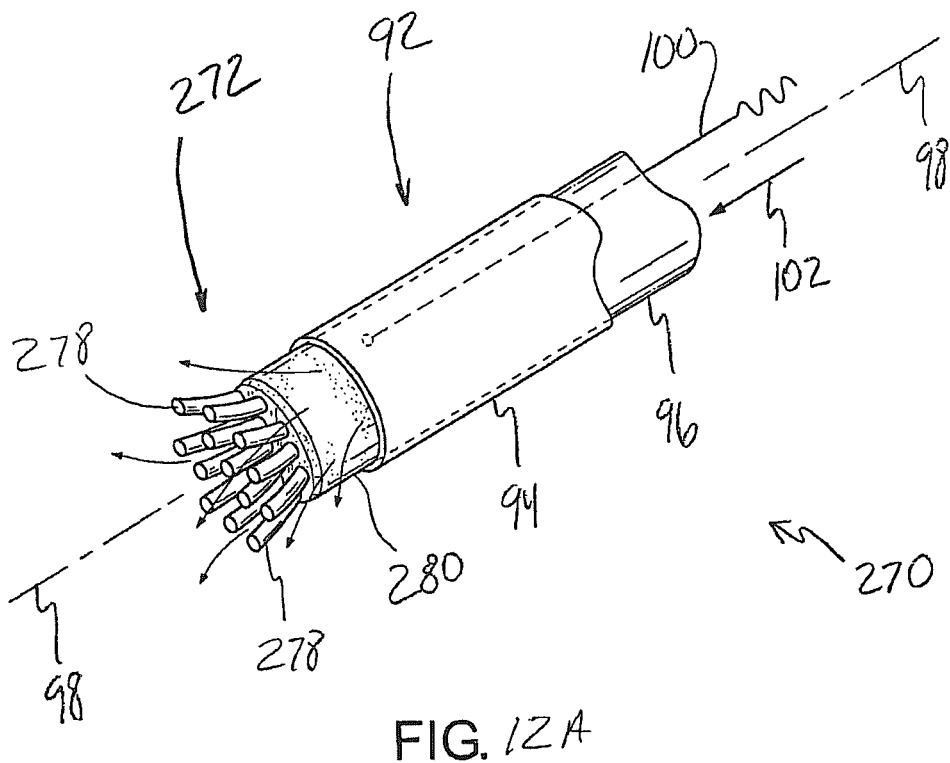
FIG. 12A is a perspective view of another embodiment of an electrode head that incorporates a plurality of electrode segments that are in the form of cantilevers and that may be defined by an electrically conductive/dissipative fabric.

The tissue electrode system 130 of FIG. 6B is illustrated as a variation of the tissue electrode system 110 of FIG. 6A, although the stepped configuration of its electrode head 132 may be used by any of the tissue electrode systems disclosed herein with the exception of the FIG. 12A embodiment. There are two main components of the electrode head 132—a fabric section 138 and a core 114. The fabric section 138 used by the electrode head 132 includes what may be characterized as a plurality of first yarn or thread segments 140 that are electrically conductive or electrically dissipative (e.g., in accordance with the first yarn segments 120 discussed above in relation to FIG. 6A), as well as what may be characterized as a plurality of the second yarn or thread segments 142 that are electrically non-conductive (e.g., in accordance with the second yarn segments 122 discussed above in relation to FIG. 6A).

There are two discrete portions of the fabric section 138 and which may be characterized as electrode segments 144a and 144b that are disposed in end-to-end relation. Each of the electrode segments 144a, 144b includes the noted first yarn segments 140 and the second yarn segments 142. Generally, the outer diameter of the electrode segment 144a is different than the outer diameter of the electrode segment 144b. In the illustrated embodiment, the outer diameter of the electrode segment 144a (the distally disposed portion of the fabric section 138) is smaller than the outer diameter of the electrode segment 144b (the proximally disposed portion of the fabric section 138).

Figure 7:
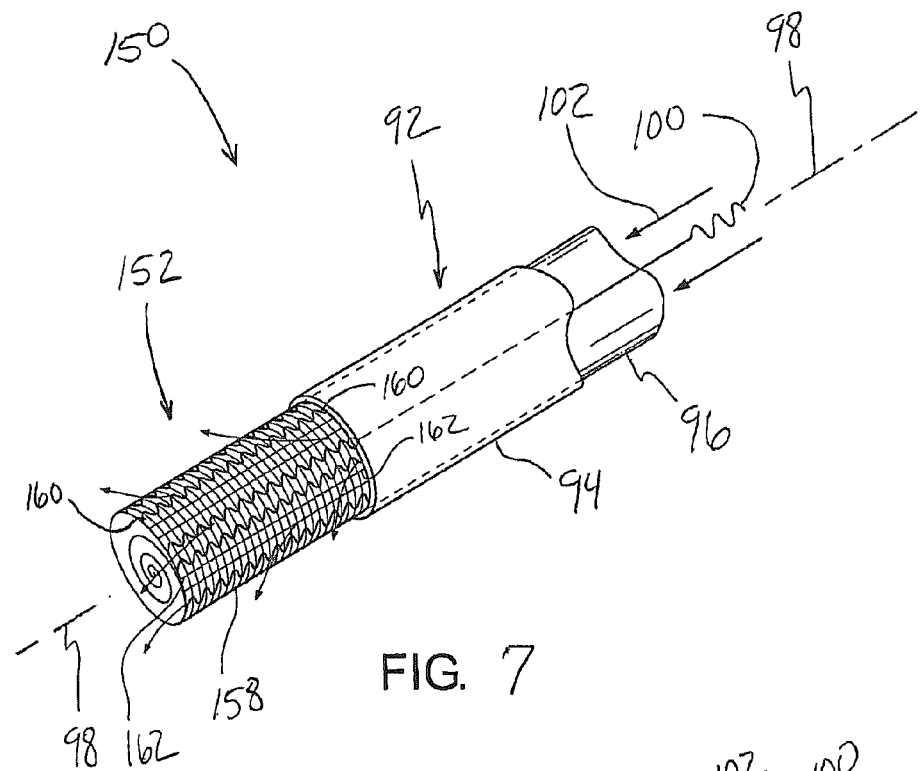
FIG. 7 is a perspective view of another embodiment of an electrode head that incorporates a plurality of electrically conductive/dissipative thread/yarn segments and electrically non-conductive thread/yarn segments that each extend at least generally along the length dimension of the electrode head.

The tissue electrode system 150 of FIG. 7 includes an electrode head 152 that in turn incorporates a fabric section 158. Instead of being wrapped around a core 114, the fabric section 158 is wrapped around itself or wrapped into a desired configuration (cylindrical in the illustrated embodiment, and as indicated by the spiral on the exposed, distal end of the electrode head 152). The fabric section 158 used by the electrode head 152 includes what may be characterized as a plurality of first yarn or thread segments 160 that are electrically conductive or electrically dissipative, as well as what may be characterized as a plurality of the second yarn or thread segments 162 that are electrically non-conductive. Generally, the various first yarn segments 160 are disposed in a common orientation with at least some of the non-conductive second yarn segments 162 (e.g., disposed in at least generally parallel relation). In this regard, the first yarn segments 160 and some of the non-conductive second yarn segments 162 extend at least generally linearly or axially along the length dimension of the electrode head 152 (e.g., at least generally parallel with the reference axis 98, or so as to define the warp of the fabric section 158). Furthermore, some of the non-conductive second yarn segments 162 are disposed or wrapped about the reference axis 98 and thereby cross or intersect with the first yarn segments 160 and those second yarn segments 162 that are similarly oriented (e.g., so as to define the weft of the fabric section 158). The various first yarn segments 160 and the various second yarn segments 162 are woven together to define the fabric section 158 (e.g., illustrated by the squiggly lines defining the first yarn segments 160). Although a pair of non-conductive second yarn segments 162 is illustrated as being disposed between adjacent pairs of first yarn segments 160, the commonly oriented first yarn segments 160 and non-conductive second yarn segments 162 may be arranged in any appropriate pattern, for instance to achieve a desired electrical field (e.g. the similarly oriented first yarn segments 160 and second non-conductive yarn segments 162 could be disposed in alternating relation).

Figure 8:
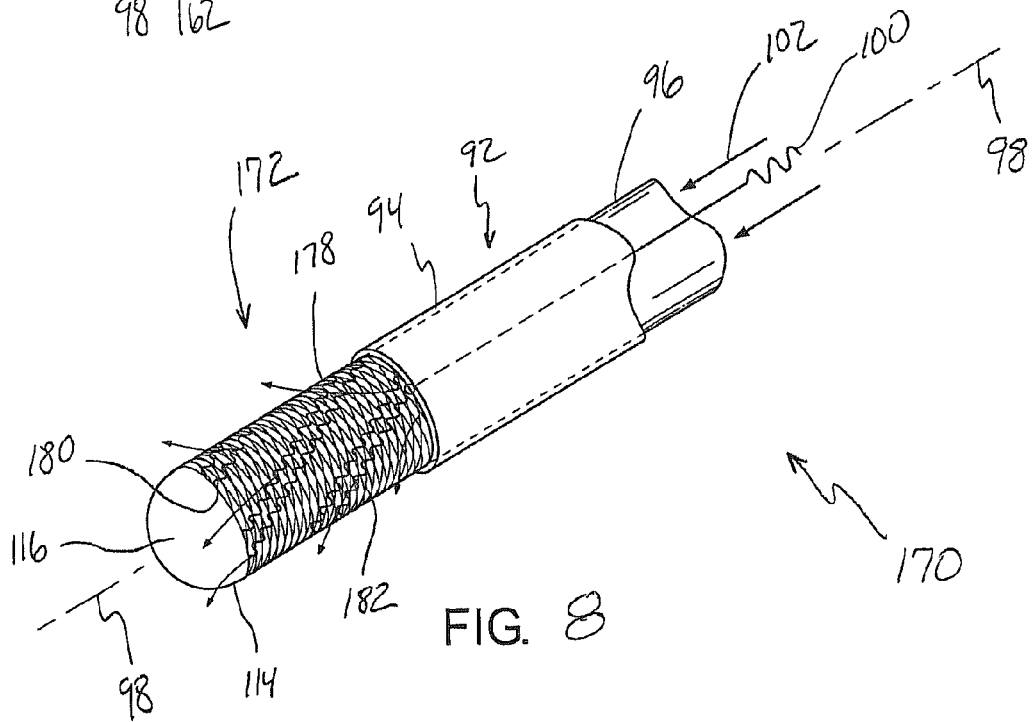
FIG. 8 is a perspective view of another embodiment of an electrode head that incorporates a plurality of electrically conductive/dissipative thread/yarn segments and electrically non-conductive thread/yarn segments that are each are wrapped about an axis that corresponds with a length dimension of the electrode head, but at different wrap angles.

The tissue electrode system 170 of FIG. 8 includes an electrode head 172. There are two main components of the electrode head 172—a fabric section 178 and a core 114. The fabric section 178 used by the electrode head 172 includes what may be characterized as a plurality of first yarn or thread segments 180 that are electrically conductive or electrically dissipative, as well as what may be characterized as a plurality of the second yarn or thread segments 182 that are electrically non-conductive. Generally, the various first yarn segments 180 are disposed in one orientation, while the various non-conductive second yarn segments 182 are disposed in a different orientation. In this regard, the first yarn segments 180 are disposed or wrapped about the reference axis 98 at one angle. Furthermore, the non-conductive second yarn segments 182 are disposed or wrapped about the reference axis 98 at a different angle than the first yarn segments 180, but still cross or intersect with the first yarn segments 180. The fabric section 178 illustrates that a first set of non-conductive second yarn segments 182 are wrapped about the reference axis 98 at one angle and that a second set of non-conductive second yarn segments 182 are wrapped about the reference axis 98 at an opposite angle. This may not be required in all instances. In any case, the various first yarn segments 180 and the various second yarn segments 122 are woven together to define the fabric section 178 (e.g., illustrated by the squiggly lines defining the first yarn segments 180).

Figure 9A:
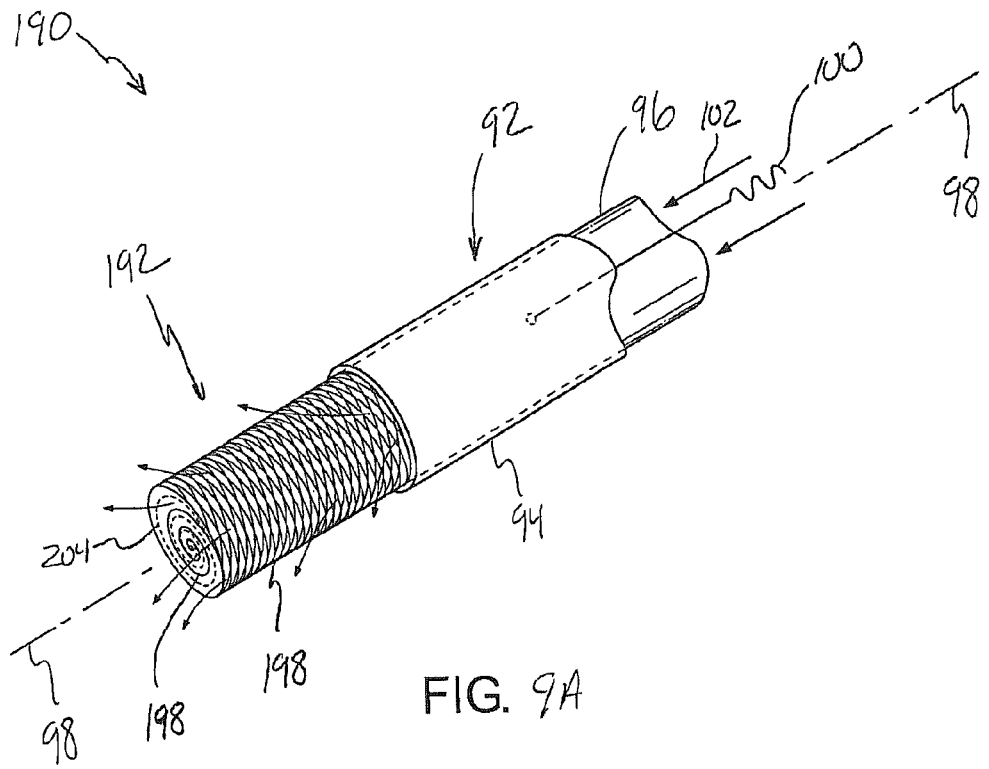
FIG. 9A is a perspective view of another embodiment of an electrode head that incorporates multiple layers that have been wrapped to define an electrode head, and where at least one of these layers is an electrically conductive/dissipative fabric.

The tissue electrode system 190 of FIG. 9A includes an electrode head 192 that in turn incorporates an electrically conductive or electrically dissipative fabric section or layer 198 and an electrically non-conductive section or layer 204. The fabric section 198 and non-conductive section 204 are disposed in interfacing relation and wrapped together into a desired configuration (at least generally cylindrical in the illustrated embodiment), with the fabric section 198 defining an exterior sidewall surface for the electrode head 192. Stated another way, the radially outermost portion of the fabric section 198 is disposed radially outwardly from the radially outermost portion of the non-conductive section 204, where a distance in the radial dimension is measured from the reference axis 98. Although the non-conductive section 204 may be in the form of a fabric, the non-conductive section 204 may be formed from any appropriate type of non-conductive material or combination of materials, and may be of any appropriate form or construction.

Figure 9B:
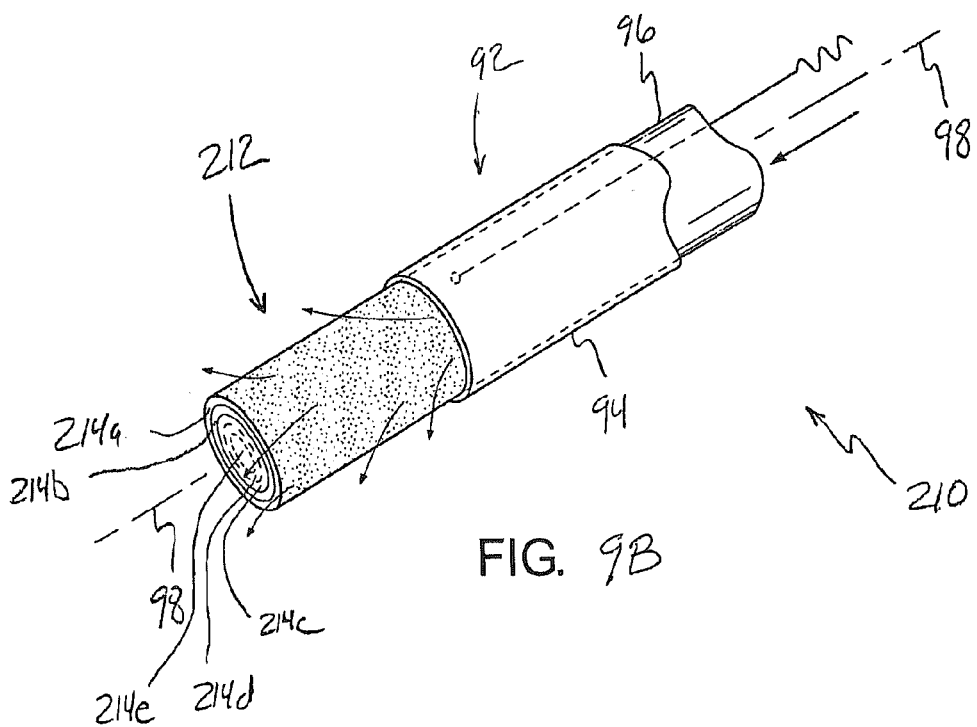
FIG. 9B is a perspective view of another embodiment of an electrode head that incorporates multiple, annular layers that define an electrode head, and where at least one of these annular layers is an electrically conductive/dissipative fabric.

The tissue electrode system 210 of FIG. 9B includes an electrode head 212 that in turn incorporates a plurality of concentrically disposed annular sections or layers 214*a-e*. Adjacent pairs of the annular sections 214*a-e* are disposed in interfacing relation in the illustrated embodiment, although a standoff could be disposed between at least one of the adjacent pairs of the annular sections 214*a-e* at one or more locations along the reference axis 98. At least one of the annular sections 214*a-e* is in the form of an electrically conductive or electrically dissipative fabric. Any number of the annular sections 214*a-e* could be in the form of an electrically conductive or electrically dissipative fabric. One or more of the annular sections 214*a-e* could also be in the form of an electrically non-conductive material (e.g., fabric). Any arrangement of electrically conductive/dissipative fabric and electrically non-conductive materials could be used for the various annular sections 214*a-e*.

Figure 10:
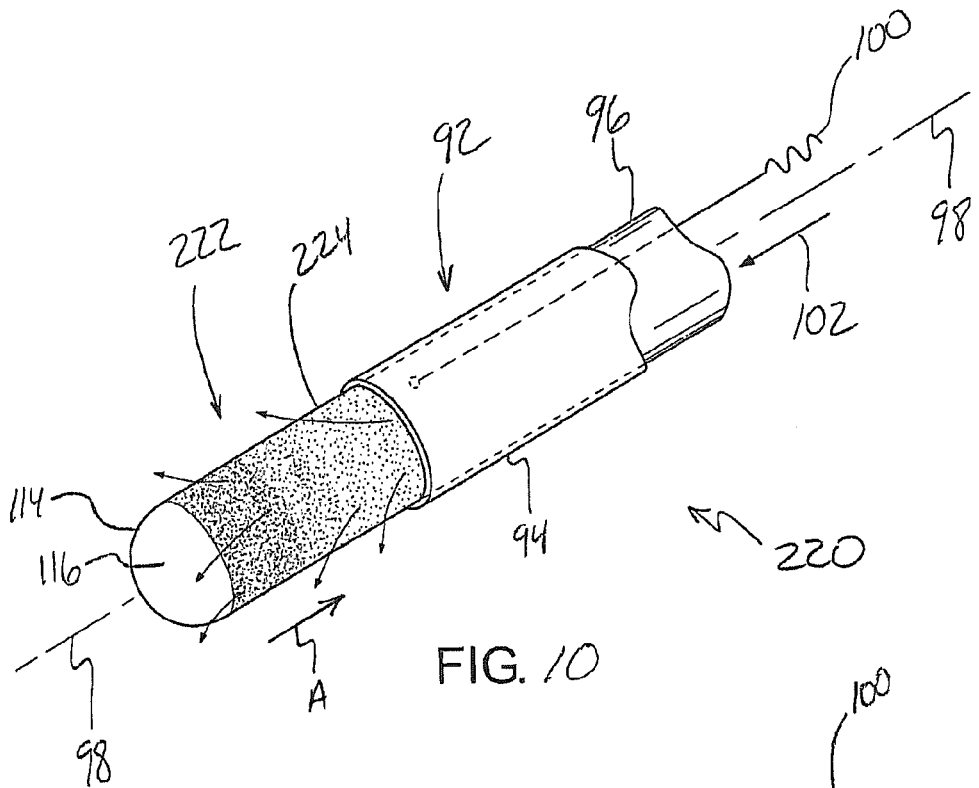
FIG. 10 is a perspective view of another embodiment of an electrode head that incorporates an electrically conductive/dissipative fabric that provides a graded electrical conductivity.

The tissue electrode system 220 of FIG. 10 includes an electrode head 222. There are two main components of the electrode head 222—a fabric section 224 and a core 114. Generally, the electrical conductivity of the fabric section 224, the hydraulic conductivity of the fabric section 224, or both, is graded or changes proceeding along the reference axis 98. In one embodiment, the electrical conductivity of the fabric section 224 decreases proceeding in the direction of the arrow A (and graphically depicted by the density of the shading provided for the fabric section 224). This variation of the electrical conductivity of the fabric section 224 may be realized in any appropriate manner. For instance, the porosity of the fabric section 224 may change proceeding along the reference axis 98. Threads of different filament count, yarns of different thread count, or both may be used to define the fabric section 224 and achieve the conductivity gradient as well. Similarly, the noted variation of the hydraulic conductivity of the fabric section 224 may be realized in any appropriate manner as well. A graded hydraulic conductivity may be achieved by modifying the porosity of the electrode head 222 and/or incorporating an anisotropically conductive fabric into the electrode head 222.

Figure 11A:
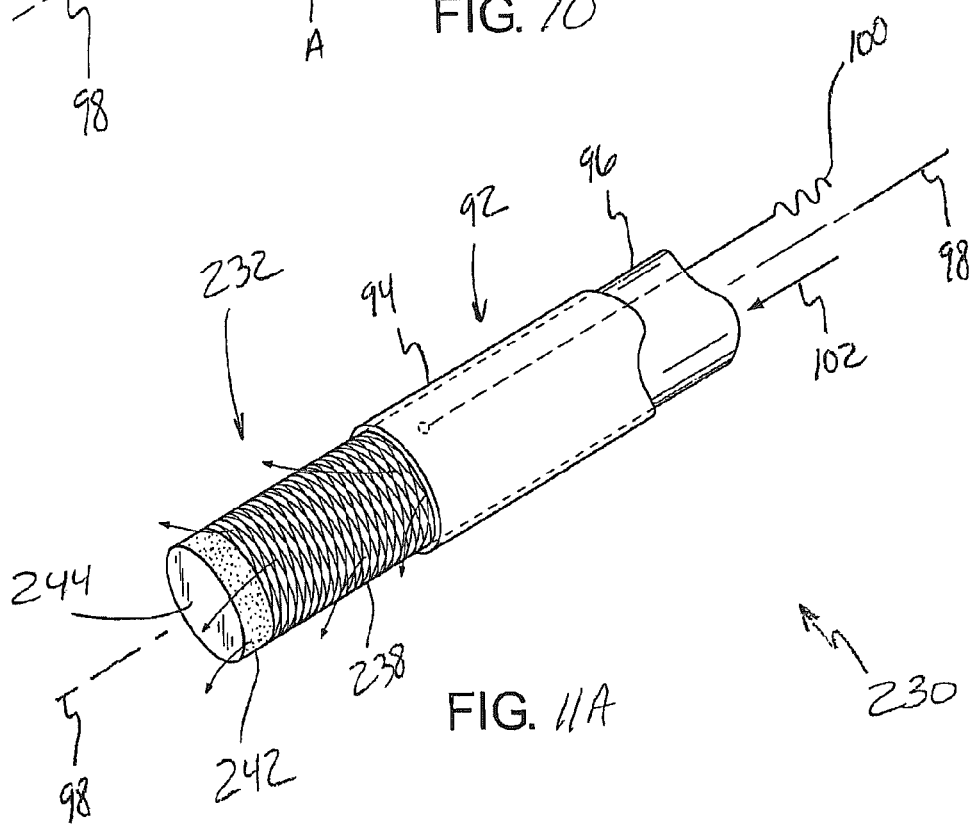
FIG. 11A is a perspective view of another embodiment of an electrode head that incorporates an electrically non-conductive distal tip, along with a proximally disposed section of an electrically conductive/dissipative fabric.

The tissue electrode system 230 of FIG. 11A includes an electrode head 232. There are two main components of the electrode head 232—an electrically conductive or electrically dissipative fabric section or electrode segment 238 and an electrically non-conductive section or electrode segment 242 that are disposed in end-to-end relation. Although the non-conductive section 242 may be in the form of a fabric, the non-conductive section 242 may be formed from any appropriate type of non-conductive material or combination of materials, and may be of any appropriate form or construction. In any case, the non-conductive section 242 is distally disposed in relation to the fabric section 238. In the illustrated embodiment, a distal end 244 of the electrode head 232 is defined by the non-conductive section 242. Stated another way, the non-conductive section 242 defines a distal tip of the electrode head 232 in the illustrated embodiment. Although the non-conductive section 242 could be in the form of a solid structure to define a solid distal end 244, the non-conductive section 242 could be defined by a wrapped configuration at least generally in accordance with the foregoing (e.g., to provide a distal end 244 have the type of configuration illustrated in FIG. 7).

The distally disposed non-conductive section 242 provides a standoff between the target tissue and the fabric section 238 in the case of the electrode head 232 of FIG. 11A. A conductive fluid may be directed to the electrode head 232 as noted above (e.g., through a flow path between the outer section 94 and inner section 96 of the body 92, and at least generally in the direction indicated by the arrow 102). This conductive fluid may carry a current from the fabric section 238 of the electrode head 232 to the target tissue, thereby creating the effect of a virtual electrode.

Figure 11B:
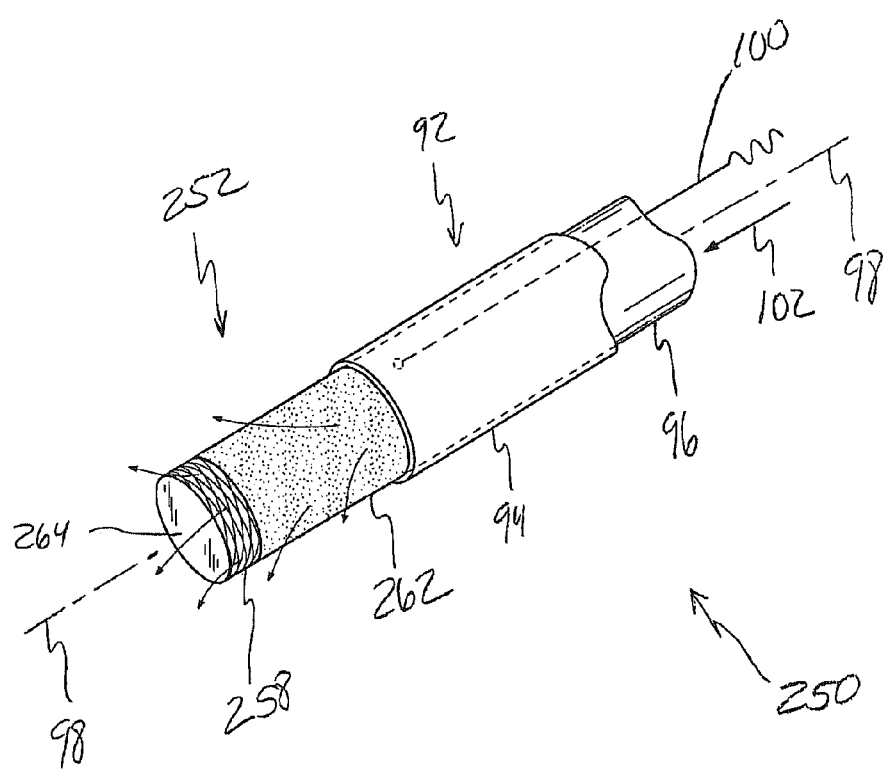
FIG. 11B is a perspective view of another embodiment of an electrode head that incorporates an electrically conductive/dissipative tip that incorporates an electrically conductive/dissipative fabric, along with a proximally disposed, electrically non-conductive section.

The tissue electrode system 250 of FIG. 11B includes an electrode head 252. There are two main components of the electrode head 252—an electrically conductive or dissipative fabric section or electrode segment 258 and an electrically non-conductive section or electrode segment 262 that are disposed an end-to-end relation. Although the non-conductive section 262 may be in the form of a fabric, the non-conductive section 262 may be foamed from any appropriate type of non-conductive material or combination of materials, and may be of any appropriate form or construction. In any case, the fabric section 258 is distally disposed in relation to the non-conductive section 262. In the illustrated embodiment, a distal end 264 of the electrode head 252 is defined by the fabric section 258, and is only schematically illustrated in FIG. 11B. This distal end 264 could be at least generally in accordance with the distal end shown in FIG. 7, or could be in the form of an appropriately shaped distal end of a core with the fabric section 258 being disposed thereabout. It should be appreciated that the fabric section 258 may also be characterized as defining a distal tip of the electrode head 232 in the illustrated embodiment.

Figure 12B:
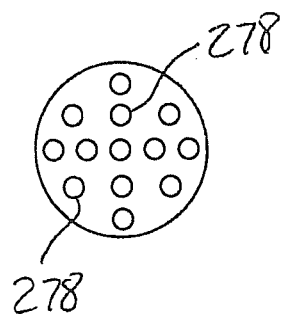
FIG. 12B is an end view of the electrode head of FIG. 12A.
Figure 12C:
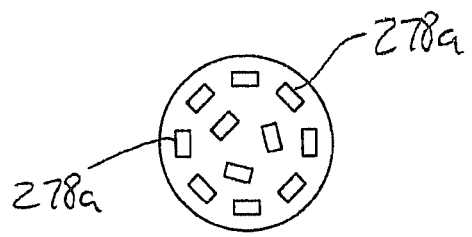
FIG. 12C is an end view of the electrode head of FIG. 12A with an alternative configuration for the electrode segments.

The tissue electrode system 270 of FIGS. 12A-B includes an electrode head 272. There are two main components of the electrode head 272—a base 280 and a plurality of electrode segments 278 that extend from the base 280. Generally, the electrode segments 278 are each in the form of a cantilever, having a fixed end (e.g., at the base 280) and a distally-disposed free end. At least some of the electrode segments 278 are disposed in different orientations. This is subject to a number of characterizations. One is that at least some of the electrode segments 278 are disposed in non-parallel relation. Another is that at least some of the electrode segments diverge relative to the reference axis 98 proceeding from the base 280 toward their respective distal end. Another is that the plurality of electrode segments 278 collectively define a splayed configuration.

Although the electrode segments 278 could be formed from any appropriate material, in one embodiment each of the electrode segments 278 includes or are defined by an electrically conductive or electrically dissipative fabric. The electrode segments 278 may be of any appropriate size, shape, and/or configuration. For instance, each electrode segment 278 could be in the form of a single thread segment or a single yarn segment, for instance in accordance with FIGS. 12A-B. Another option would be for each of the fabric sections 278 to be in the form of a fabric section, such as the fabric sections 278a illustrated in FIG. 12C.

The various electrode segments 278 may be disposed in any appropriate arrangement. Each of the various electrode segments 278 may be equally spaced from each other. Two or more different spacings between adjacent electrode segments 278 may be utilized as well. In one embodiment, the electrode head 292 utilizes an at least substantially constant density for the various electrode segments 278. Another embodiment utilizes a varied density for the various electrode segments 278.

Figure 13:
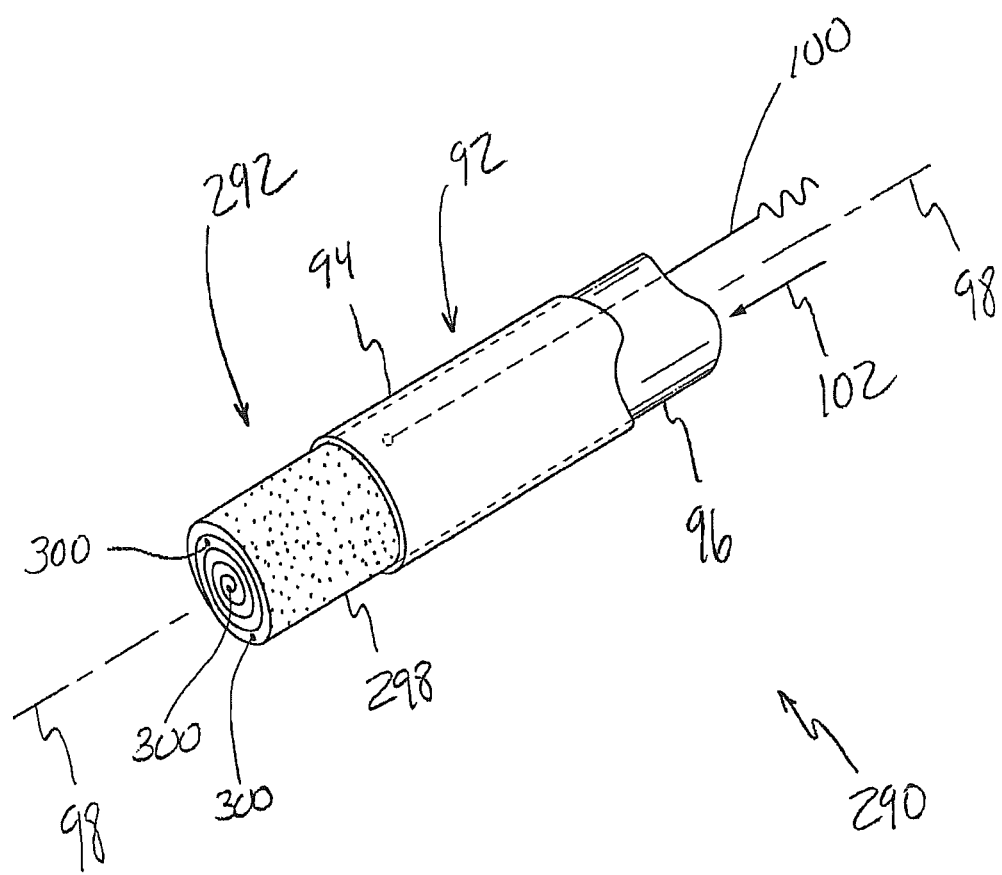
FIG. 13 is a perspective view of another embodiment of an electrode head that incorporates an electrically conductive/dissipative fabric and a plurality of sensors.

The tissue electrode system 290 of FIG. 13 includes an electrode head 292, that in turn includes an electrically conductive or electrically dissipative fabric section 298. The electrode head 292 further includes one or more sensors 300. Three sensors 300 are illustrated in relation to the electrode head 292, although any number of sensors 300 may be utilized and may be disposed at any appropriate location. Each sensor 300 may be of any appropriate size, shape, configuration, and/or type, and furthermore may provide any appropriate function or combination of functions. For instance, a sensor 300 may be provided to monitor temperature (e.g., an electrode head-tissue interface temperature), a sensor 300 may be provided to monitor pressure (e.g., a pressure being exerted by the electrode head 292 on the tissue), or a sensor 300 may be used for situ lesion identification and characterization (e.g., using fiber optics, ultrasound, or both). One or more of these sensors 300 may be utilized by any of the electrode heads disclosed herein.

The electrode heads described herein may be used with any appropriate type of electrode. For instance, each of these electrode heads may be integrated with a catheter electrode. Another option is for each of these electrode heads to be used by a ground patch or the like that interfaces with the patient's skin (e.g., interfaces with an exterior surface of the patient). Each such electrode head may also provide any appropriate function or combination of functions. One embodiment has the electrode head providing an active function, such as tissue ablation or tissue mapping. Another embodiment has the electrode head configured for a passive function, such as for use by a return electrode. Each electrode head may direct electrical energy to a single location (e.g., for spot tissue ablation), or may apply electrical energy to tissue while being moved relative to the tissue (e.g., to create a linear lesion).

Each of the electrode heads disclosed herein may be used in a dry electrode configuration, or alternatively in a wet electrode configuration. With regard to a wet electrode configuration, any appropriate fluid may be utilized. In one embodiment, the fluid is electrically conductive. Representative fluids for a wet electrode configuration include without limitation saline, radioopaque solutions, and liquid drugs. Any appropriate flow rate may be provided to any of the electrode heads disclosed herein as well. In one embodiment, a flow rate of no more than about 30 ml/minute may be provided to any of the electrode heads disclosed herein, and which may be suitable based upon the use of one or more fabric sections.

Although various embodiments of this invention have been described above with a certain degree of particularity, those skilled in the art could make numerous alterations to the disclosed embodiments without departing from the spirit or scope of this invention. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other unless otherwise noted. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A tissue electrode system, comprising:
   an elongated catheter body having a distal end adapted for disposition within a patient body and having at least a first fluid conduit extending through a portion of said elongated catheter body and exiting though said distal end of said elongated catheter body;
   a multilayered fabric electrode having a generally cylindrical shape with a rearward peripheral edge, wherein an entirety of the rearward peripheral edge is fixedly attached to said distal end of said elongated catheter body and around said first fluid conduit and being free of internal support, wherein said multilayered fabric electrode is cantilevered from said distal end of said elongated catheter body, said multilayered fabric electrode including:
     a substantially cylindrical first fabric layer having first and second sets of woven threads, wherein at least a portion of said substantially cylindrical first fabric layer is electrically conductive or electrically dissipative and is adapted to exchange electrical energy with tissue, and wherein at least part of said substantially cylindrical first fabric layer is electrically connectable with an electrical energy source; and
     a substantially cylindrical second fabric layer having first and second sets of woven threads, wherein said substantially cylindrical second fabric layer is at least partially disposed within an interior of said substantially cylindrical first fabric layer wherein said first and second substantially cylindrical fabric layers are porous to permit fluid through the distal end of the elongated catheter body to pass into and through said multilayered fabric electrode.

2. The tissue electrode system of claim 1, wherein said first and second substantially cylindrical fabric layers comprise a single fabric sheet rolled upon itself into a generally cylindrical configuration, wherein said first substantially cylindrical fabric layer forms an outside surface of said multilayered fabric electrode.

3. The tissue electrode system of claim 2, further comprising:
an electrically non-conductive sheet disposed between adjacent rolls of said first and second substantially cylindrical fabric layers.

4. The tissue electrode system of claim 1, wherein said first substantially cylindrical fabric layer comprises a first annular fabric layer and said second substantially cylindrical fabric layer comprises a second annular fabric layer.

5. The tissue electrode system of claim 4, wherein said second annular fabric layer is electrically conductive or electrically dissipative and wherein at least part of said second annular fabric layer is electrically connectable with the electrical energy source.

6. The tissue electrode system of claim 5, further comprising:
an electrically non-conductive annular layer disposed between said first annular fabric layer and said second annular fabric layer.

7. The tissue electrode system of claim 1, wherein an entirety of said substantially cylindrical first fabric layer is electrically conductive.

8. The tissue electrode system of claim 1, wherein said substantially cylindrical first fabric layer comprises both an electrically conductive material and an electrically dissipative material.

9. The tissue electrode system of claim 8, wherein said first and second sets of woven threads of said substantially cylindrical first fabric layer comprises a first set of electrically conductive or electrically dissipative threads and a second set of electrically non-conductive threads.

10. The tissue electrode system of claim 1, wherein said multilayered fabric electrode comprises first and second segments disposed in end-to-end relation, wherein said first segment comprises said first substantially cylindrical fabric layer and said second segment comprises said second substantially cylindrical fabric layer.

11. The tissue electrode system of claim 10, wherein at least a portion of said second segment is disposed distally relative to said first segment.

12. The tissue electrode system of claim 1, wherein a hydraulic conductivity of said multilayered fabric electrode varies along a length dimension of said multilayered fabric electrode.

13. The tissue electrode system of claim 1, wherein an electrical conductivity of said multilayered fabric electrode varies along a length dimension of said multilayered layered fabric electrode.

* * * * *